(12) United States Patent
Bachand

(10) Patent No.: US 6,375,897 B1
(45) Date of Patent: Apr. 23, 2002

(54) URINE COLLECTION CUP

(75) Inventor: Steven S. Bachand, Laguna Niguel, CA (US)

(73) Assignee: Ansys Technologies, Inc., Lake Forest, CA (US)

( * ) Notice: Subject to any disclaimer, the term of this patent is extended or adjusted under 35 U.S.C. 154(b) by 0 days.

(21) Appl. No.: 09/503,297

(22) Filed: Feb. 14, 2000

(51) Int. Cl.⁷ ................................................ G01N 31/22
(52) U.S. Cl. ............................ 422/58; 422/55; 422/56; 422/61; 422/102; 422/947; 436/169; 600/573; 600/584; 604/318; 604/404
(58) Field of Search .............................. 422/55, 56, 58, 422/61, 102, 68.1, 947; 436/164, 165, 169; 600/573, 574, 584; 604/318, 404

(56) References Cited

U.S. PATENT DOCUMENTS

| | | | | |
|---|---|---|---|---|
| 3,774,455 A | * | 11/1973 | Seidler et al. ................. | 73/444 |
| 3,849,256 A | * | 11/1974 | Linder ...................... | 435/287.7 |
| 4,473,530 A | * | 9/1984 | Villa-Real .................... | 422/58 |
| 5,119,830 A | * | 6/1992 | Davis ........................ | 600/584 |
| 5,352,410 A | * | 10/1994 | Hansen et al. ................. | 422/58 |
| 5,403,551 A | * | 4/1995 | Galloway et al. .............. | 422/58 |
| 5,500,375 A | * | 3/1996 | Lee-Own et al. ............ | 436/574 |
| 5,501,837 A | * | 3/1996 | Sayles ......................... | 422/58 |
| 5,595,187 A | * | 1/1997 | Davis ......................... | 600/584 |
| 5,728,587 A | * | 3/1998 | Kang et al. .................. | 436/518 |
| 5,789,255 A | * | 8/1998 | Yu ............................. | 436/95 |
| 5,800,785 A | * | 9/1998 | Bochner ..................... | 422/101 |
| 5,916,815 A | * | 6/1999 | Lappe ......................... | 436/92 |
| 5,932,480 A | * | 8/1999 | Maruo et al. ................. | 436/66 |
| 5,976,895 A | * | 11/1999 | Cipkowski .................. | 436/518 |

* cited by examiner

Primary Examiner—Maureen M. Wallenhorst
(74) Attorney, Agent, or Firm—Walter A. Hackler

(57) ABSTRACT

A urine collection cup device is provided including a clear plastic cup, a reagent strip disposed against an inner surface of the cup and adhered thereto by means of a plastic laminate or adhesive member. An aperture is provided in the adhesive member on a sample introduction end of the reagent strip to enable a fluid sample to be introduced onto the reagent strip. By capillary action the fluid migrates up the reagent strip and causes a visible indication of test validity and test results. A second aperture covered with a hydrophobic material is provided adjacent the reagent strip end to enable air to vent from the strip while preventing fluid specimen from entering therein.

10 Claims, 1 Drawing Sheet

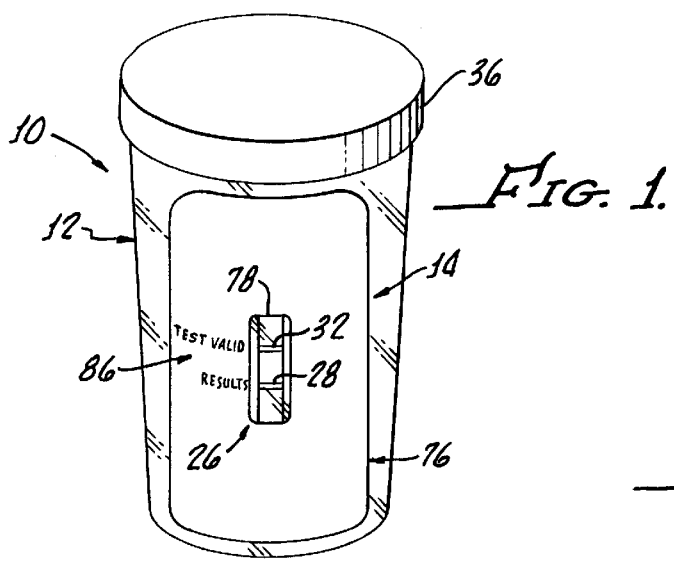
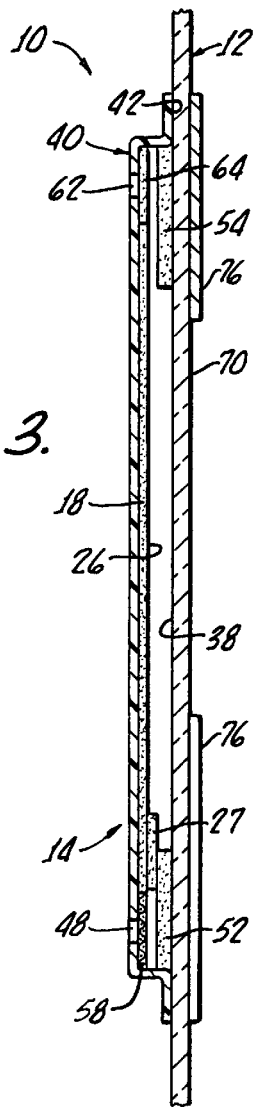
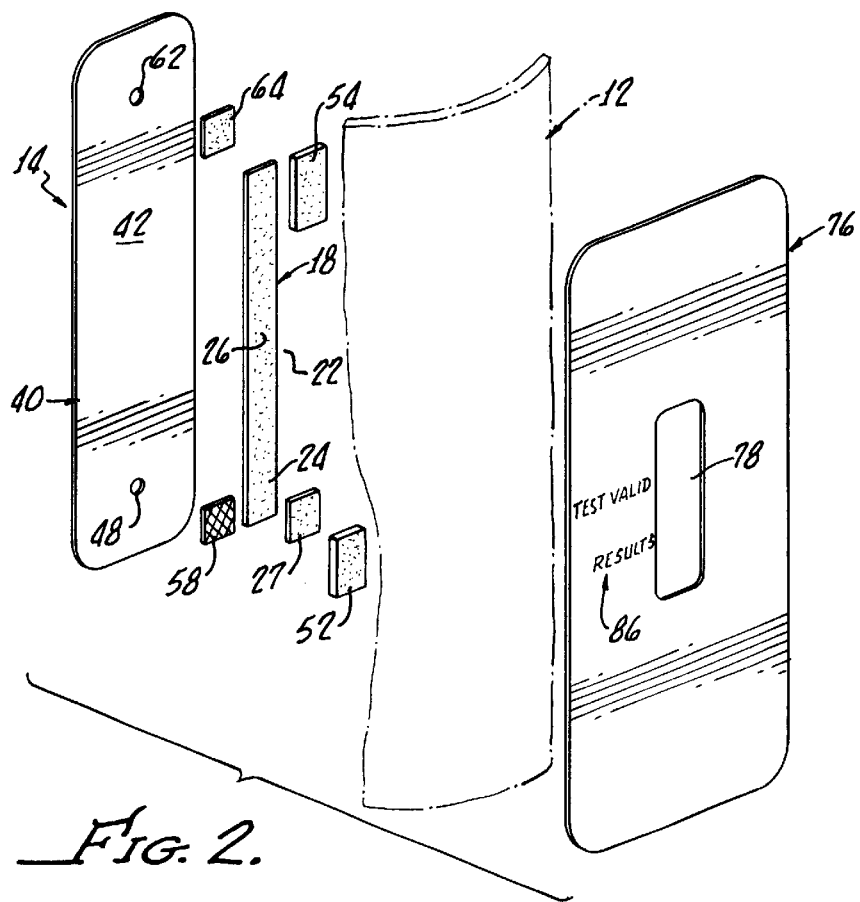

URINE COLLECTION CUP

The present invention generally relates to diagnostic testing devices and more specifically relates to a device for containing a fluid sample, for example a urine specimen, and conducting diagnostic testing of the contained fluid sample.

Assay testing of bodily fluids, for example blood, urine and salivary fluid, is well known but serious disadvantages are presented by conventional devices which expose a technician to physical contact with the fluid. For example a common test performed by health care workers involves testing a maternity patient for signs of gestational diabetes. The patient collects a sample of urine in a sterile cup and closes the cup with a lid. With gloved hands, the health care worker removes the lid and manually immerses an end of a diagnostic test strip into the urine sample. The worker then manually removes the test strip from the sample, and may perform analysis of any color change or other visible indicia on the test strip. Although the risk of contamination between the patient and the health care worker may be small in this situation, there is always some risk involved when the health care worker is exposed to an open container of bodily fluid. Further, there is also a risk of cross contamination between different patients when multiple tests are being performed. Because the test strip is handled separately from the container, there is a potential risk of test results being misidentified between patients.

Other diagnostic test procedures, for example immunoassay testing procedures involve using a pipette or other device to manually extract a small amount of a fluid sample from an open collection container, thus also presenting a risk of contamination or exposure to disease.

Conventional devices have been developed to overcome these and other disadvantages of such open-cup fluid testing procedures. In U.S. Pat. No. 5,501,837 to Sayles, a specimen testing system is disclosed which utilizes a cup having a cover lid. Within the cover lid are contained one or more reagent membrane strips used for conducting chromatographic immunoassay testing of a fluid deposited in the cup when the cup is inverted. Although offering an advantage over open-cup test procedures, the Sayles invention, and others similar thereto, are not significantly cost effective to manufacture as they require rotatable components, assembling of reagent strips within a lid assembly. Furthermore, the method of use of the Sayles invention requires the cup to be inverted, thus increasing a risk of the fluid leaking therefrom, for example if the cover lid has not been sufficiently secured.

There is still a need for an economical, easy to manufacture device which reduces or substantially eliminates the risks associated with diagnostic testing of bodily fluids.

SUMMARY OF THE INVENTION

The present invention provides a cost-effective, easy to manufacture and highly reliable device for collecting and testing bodily fluids, such as urine for example. The device is designed to substantially overcome the disadvantages of prior devices and procedures, including reducing risk of specimen contamination and injury to health care workers.

A diagnostic device, in accordance with the present invention, for collecting and testing a fluid specimen, generally comprises a cup or other container suitable for holding a fluid specimen, particularly a bodily fluid specimen, for example urine, and test means, sealed to the cup, for indicating a presence of at least one specific component of the fluid specimen.

More particularly, the test means includes a reagent strip, for example a conventional reagent strip, including a portion for displaying visible indicia of test results. An adhesive member overlying the reagent strip is provided for sealing the strip to an inner surface of the cup. The reagent strip may be positioned on an inner surface of the cup, preferably with the test results portion thereof facing the inner surface of the cup and being visible through the outer surface of the cup. For example, at least a portion of the cup is clear or sufficiently transparent to enable one to see test results on the reagent strip. The adhesive member may be an adhesive plastic label that provides a fluid tight seal around a periphery of the reagent strip against the inner surface of the cup. The fluid sample collected in the cup is prevented from contacting the reagent strip, with the exception of the sample introduction end or portion of the test strip, which is exposed to the fluid sample by means of a cut-out portion defined in the adhesive label. More particularly, a die cut aperture in the adhesive member provides means for introducing the fluid specimen contained in the cup and onto the sample introduction end, or other appropriate portion of the the reagent strip to cause the fluid sample to migrate along the reagent strip by capillary action. The sample introduction end may include a sample pad for absorbing the fluid specimen and saturating the sample introduction end of the reagent strip and a conjugate pad.

In one feature of the present invention, a small filter may be provided on the sample introduction end of the reagent strip, for example a filter paper disposed over the adhesive label aperture, in order to pre-filter the fluid sample prior to its entry into the sample pad.

As the seal provided by the adhesive label about the reagent strip is substantially fluid tight, preferably means are provided for venting air from the reagent strip as the fluid sample migrates along the reagent strip. For example, in one advantageous embodiment of the invention, the means for venting comprises a second aperture in the adhesive member, the second aperture being covered with a hydrophobic material adapted to prevent fluid flow into the reagent strip while enabling air flow out of the reagent strip.

It is to be appreciated that in one broad embodiment of the invention, the container is not considered as a part of the invention, and the invention may comprise the test means as being adapted to be sealed or adhered to any suitable cup or container.

In another feature of the invention, the test device may further comprise a substantially opaque member providing means for masking or concealing the test means from view through the outer surface of the cup means, while also revealing the test results portion of the reagent strip. For example, the opaque member may comprise an adhesive label adhered to the outer surface of the container and including a cut-out portion or clear window exposing the test results through the outer surface of the cup. The opaque label may also include information inscribed thereon, for example adjacent the window, for enabling identification of test results on the reagent strip.

BRIEF DESCRIPTION OF THE DRAWINGS

The objects and advantages of the present invention may be more clearly understood and appreciated with respect to the following detailed description when considered in conjunction with the accompanying Figures in which:

FIG. 1 shows a perspective view of an embodiment of the present invention including a collection cup and a test device adhered thereto;

FIG. 2 shows an exploded view of the embodiment shown in FIG. 1 with a portion of the container shown in phantom line; and FIG. 3 shows a cross-sectional view of the embodiment shown in FIG. 1.

DETAILED DESCRIPTION

Turning now to FIG. 1, a fluid specimen collection and testing device 10 in accordance with the present invention is shown in perspective view. The device 10 generally comprises a cup 12 providing means for containing a fluid sample or specimen, and a test device 14, sealed to the cup 12, for indicating a presence of at least one specific component of the fluid specimen.

It is noted that the present invention 10 shown and hereinafter described was designed for collection and testing or bodily fluids, and specifically urine. However, with appropriate modification to the presently described device, such modifications being considered as in the scope of the present invention, the device may be made suitable for collection and testing of other fluids, for example blood and other bodily fluids.

Turning now as well to FIG. 2, the test device 14 more specifically includes a reagent strip 18. The structure of the reagent strip 18 may be conventional, for example the strip 18 may comprise an absorbent membrane 22 including a sample introduction end or portion 24, and a test results portion 26. For example, a conjugate pad 27 containing a suitable conjugate is provided on the sample introduction end 24. In addition, the test results portion 26 may have has incorporated therein a specific reagent (not shown) which manifests a detectable response, for example a color change 28 (shown in FIG. 1), in the presence of a specific component of the sample fluid that is absorbed by the membrane 22. Further, a validity indicator 32 may also be provided on the membrane 22 to provide a visual indication that a sufficient amount of fluid sample has been absorbed by the membrane 22 to produce a valid test result. Test strips suitable for use with the present invention are well known and thus will not be described in greater detail herein.

The cup 12 is preferably made of plastic or glass and is transparent, clear, or includes at least a portion of which is substantially transparent or clear. The cup 12 includes or is adapted to include a lid 36 that is threadably engageable to the cup 12 to provide a substantially fluid tight seal therebetween.

As shown in FIGS. 2 and 3, the test device 14 further comprises means for sealing the reagent strip 18 to a surface of the cup 12. Preferably, the reagent strip 18 is sealed to an inner surface 38 of the cup 12. The means for sealing the reagent strip 18 may comprise an adhesive member 40 overlaying the reagent strip 18 and including an adhesive surface 42 adapted to be adhered, in a fluid tight engagement, to the inner surface 38 of the cup 12. The adhesive member 40 may comprise for example a plastic laminate.

Means, defined by a cut-out portion, or die cut aperture 48, hereinafter sometimes referred to as "first aperture 48", in the adhesive member 40, is provided for introducing the fluid sample, contained in the cup 12, onto the sample introduction end 24.

Preferably, an absorbent sample pad 52 disposed immediately beneath the aperture 48, may be provided as an absorbent interface between the container surface 38 and the conjugate pad 27. Similarly, an end pad 54 made of a suitable absorbent material may be provided between the reagent strip 18 and the container surface 38. The pads 52, 54 prevent the reagent strip 18 from becoming excessively saturated by the fluid sample.

In one advantageous aspect of the present invention 10, means are provided for filtering the fluid specimen prior to its entry onto the sample pad 52. More particularly, a small filter paper 58, or the like, may be placed over the sample introduction end 24 of the test strip 18 and adhered to the adhesive member 40, covering the first aperture 48.

In another advantageous aspect of the present invention 10, means for venting air from the reagent strip 18 is provided. For example, a second aperture 62 or cut-out defined in the adhesive label 40 provides means for venting air from the reagent strip 18 as the fluid sample migrates upward along the reagent strip 18. This feature promotes efficient migration of the fluid through the membrane 22. Preferably, the means for venting may also include a hydrophobic member 64 disposed over the vent aperture 62, wherein the hydrophobic member 64 comprises any suitable hydrophobic material known in the art. The hydrophobic member prevents fluid flow from entering the reagent strip 18 while enabling air flow out of the reagent strip 18.

Preferably, as shown in FIGS. 2 and 3, the device 10 is assembled with the test results portion 26 of the reagent strip 18 facing the inner surface 38 of the cup 12 and applied thereto by means of the surrounding adhesive member 40. As mentioned hereinabove the cup 12 is preferably a clear, or substantially transparent, plastic or glass container. The test results displayed on the reagent strip 18 are therefor visible through an outer surface 70 of the cup 12, as shown in FIG. 1.

The test device 10 of the present invention may also include a substantially opaque, adhesive label 76, for masking or concealing working portions of the test means 14 from view. The label 76 may be applied to the outside surface 70 of the cup 12. Means, such as a window 78 or die cut portion, for revealing the test results portion 26 of the reagent strip 18 is provided. Indicia 86 may be inscribed on the label 76 adjacent the window 78 to display information, for example "test valid" and "results" as shown in FIGS. 1 and 2.

Other alternative assemblies in accordance with the invention are contemplated. For example, it is contemplated that with appropriate modification, the adhesive label 76 may be applied directly to the adhesive member 40, with the reagent strip 18 and pads 52 and 54 disposed between the two adhesive member 40 and adhesive label 40. In this case, the adhesive label 76 may be applied to the inner surface 38, rather than the outer surface 70, of the container 12.

It is to be appreciated that an embodiment of the present invention considered within the scope of the invention, may include the test device 14 without the cup 12. The test device 14 may be sold and packaged independently of the means for containing the fluid sample. Alternative to the container 12 shown in FIG. 1, other container sizes and shapes may be used. In addition, it is contemplated that several different test devices in accordance with the invention, and adapted to test for different components of a fluid sample, may be applied to a single container for enabling multiple tests to be performed on an individual fluid specimen.

Accordingly, the present invention 10 as hereinabove described and shown, overcomes the disadvantages of prior collection and testing devices. A description of the operating mode of the device 10 is as follows. As urine is collected into the cup 12, the test begins to run as the urine level rises to contact the sample introduction aperture 48 adjacent the bottom of the inner adhesive member 40. The test therefor is "self-starting" and does not require the user to perform any tasks, other than to collect the urine sample inside the cup 12. As the urine migrates through the test results portion 26 of the strip 18, a "test valid/complete" result is observable through the window 78 in the outer adhesive label 76, and the test results are read. The device 10 substantially eliminates risk of physical contact between a health care worker/ technician, or other user, and the bodily fluid inside the cup 12. For example, a patient can collect the urine and seal the cup 12 by means of the cap 12 before delivering the cup 12 to the user. The present device does not require the user to open the cap 36 to perform analysis of the sample.

Although there has been hereinabove described a urine collection device and cup, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

For example, rather than a single reagent strip, the test 10 could be modified to perform multiple tests on a single sample of fluid in the cup by including multiple reagent strips and/or analytes.

What is claimed is:

1. A fluid specimen collection device comprising:
    a transparent cup having an inner surface for containing a fluid specimen;
    a reagent strip for indicating a presence of at least one specific component of said fluid specimen;
    an adhesive member for encapsulating the strip against said inner surface;
    a first aperture through said adhesive member and aligned with a first end of said reagent strip for introducing said fluid specimen to the first end of the strip;
    a second aperture through said adhesive member and aligned with a second end of said reagent strip for venting air from the reagent strip in a direction transverse to the longitudinal axis of the strip; and
    a pair of end pads, disposed between the cup inner surface and the strip at the strip first and second ends, for providing a spaced apart relationship between the strip and the cup inner surface.

2. The device according to claim 1 further comprising a filter, separate from said reagent strip and disposed between said reagent strip and said first aperture, for filtering said fluid specimen before entry onto the first end of the strip.

3. The device according to claim 2 further comprising a hydrophobic member, separate from said reagent strip and disposed between said reagent strip and said second aperture, for preventing fluid flow into said reagent strip while enabling air flow out of said reagent strip through said second aperture.

4. The device according to claim 3 further comprising a conjugate pad disposed at the first end of the strip.

5. The device according to claim 1 wherein said end pads are absorbent in order to prevent said reagent strip from becoming saturated with fluid specimen.

6. The device according to claim 5 further comprising a conjugate pad disposed at the first end of the strip.

7. A fluid specimen collection device comprising:
    a transparent cup having an inner surface for containing a fluid specimen;
    a reagent strip, having a first and a second end, for indicating a presence of at least one specific component of said fluid specimen;
    an adhesive member for encapsulating the strip against said inner surface
    a first aperture through said adhesive member and aligned with a first end of said reagent strip for introducing said fluid specimen to the first end of the strip; and
    a pair of end pads, disposed between the cup inner surface and the strip at the strip first and second ends, for providing a spaced apart relationship between the strip and the cup inner surface.

8. The device according to claim 7 further comprising a filter, separate from said reagent strip and disposed between said reagent strip and said first aperture, for filtering said fluid specimen before entry onto the first end of the strip.

9. The device according to claim 7 wherein said end pads are absorbent in order to prevent said reagent strip from becoming saturated with fluid specimen.

10. The device according to claim 9 further comprising a conjugate pad disposed at the first end of the strip.

* * * * *